United States Patent [19]

Czernichow

[11] Patent Number: 5,241,869
[45] Date of Patent: Sep. 7, 1993

[54] DEVICE FOR TAKING A FLUID SAMPLE FROM A WELL

[75] Inventor: Jean A. Czernichow, Chatenay Malabry, France

[73] Assignee: Gaz De France, France

[21] Appl. No.: 575,556

[22] Filed: Aug. 30, 1990

[30] Foreign Application Priority Data

Aug. 31, 1989 [FR] France ............... 89 11452

[51] Int. Cl.$^5$ .............. E21B 47/00; G01N 1/14; G01N 1/24
[52] U.S. Cl. .................. 73/864.52; 73/155; 73/864.63; 166/264
[58] Field of Search .............. 73/152, 153, 863.01, 73/863.33, 864.51, 864.62, 864.67, 864.91, 155, 864.52, 864.63; 166/264

[56] References Cited

U.S. PATENT DOCUMENTS

| | | | |
|---|---|---|---|
| 2,249,815 | 7/1941 | Ennis | 73/153 |
| 2,370,818 | 3/1945 | Silverman | 73/152 |
| 2,852,081 | 9/1958 | Lebourg | 166/169 |
| 2,927,641 | 3/1960 | Buck | 166/64 |
| 2,978,688 | 4/1961 | Rumble | 73/152 |
| 3,079,973 | 3/1963 | Le Bus | 73/152 |
| 3,095,930 | 7/1963 | Kisling | 166/264 |
| 3,104,542 | 9/1963 | Scoggins | 73/863.01 |
| 3,288,210 | 11/1966 | Bryant | 73/152 |
| 3,318,145 | 5/1967 | Lynn et al. | 73/152 |
| 3,957,117 | 5/1976 | Dole | 166/264 |
| 3,986,553 | 10/1976 | Klyen | 166/264 |
| 4,370,886 | 2/1983 | Smith, Jr. et al. | 73/153 |
| 4,417,622 | 11/1983 | Hyde | 73/864.52 |
| 4,553,428 | 11/1985 | Upchurch | 73/152 |
| 4,737,636 | 4/1988 | Smith, Jr. | 250/269 |
| 4,811,599 | 3/1989 | Johnson et al. | 73/155 |
| 4,940,088 | 7/1990 | Goldschild | 73/864.62 |

FOREIGN PATENT DOCUMENTS

| | | |
|---|---|---|
| 358791 | 4/1929 | Belgium . |
| 2053822 | 6/1972 | Fed. Rep. of Germany . |
| 2123178 | 9/1972 | France . |
| 148696 | 7/1985 | France . |

Primary Examiner—Hezron E. Williams
Assistant Examiner—George M. Dombroske
Attorney, Agent, or Firm—Ostrolenk, Faber, Gerb & Soffen

[57] ABSTRACT

A device for taking samples of a gaseous fluid from a well at a given depth. The device includes a control portion having a probe which may be removably assembled to one end of a bottle portion. The probe includes an inner space communicating at one end with the outside through a passage-way for the inflow of the fluid within this space into the sampler and at another end through an inner channel with the sample receiving chamber in the bottle. A channel closure valve is mounted in the probe and provided with an actuator remote-controlled from the surface. A remote-controlled motor with a rotary output shaft extends in parallel relation to the axis of the device. A device for transforming the rotary motion of the motor shaft into an axial motion of a rod displaceable in the direction of the axis of the device is provided. A sample-taking valve, comprising a movable element for opening and closing the valve, is mounted in axially displaceable relationship on this rod.

13 Claims, 3 Drawing Sheets

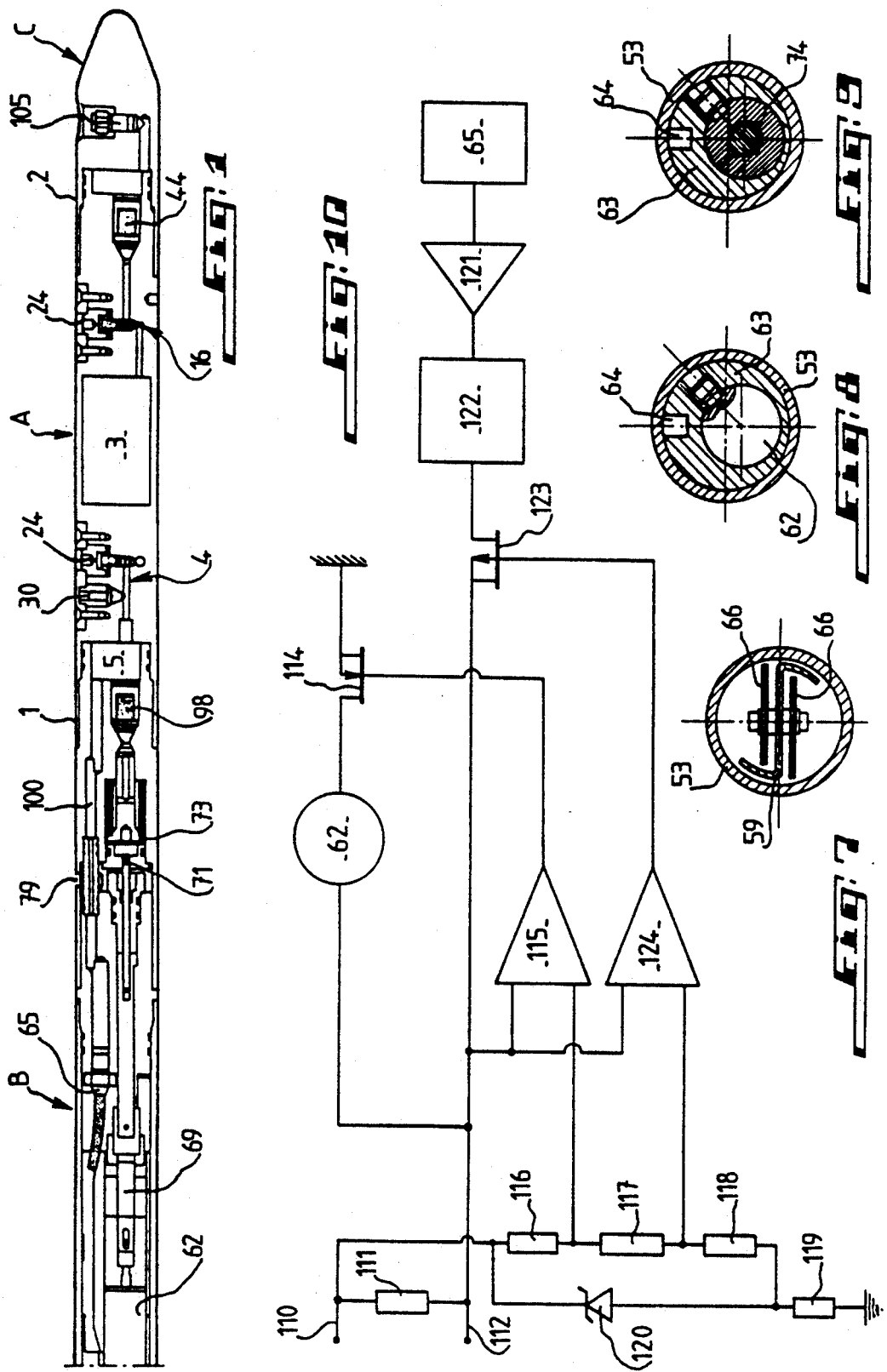

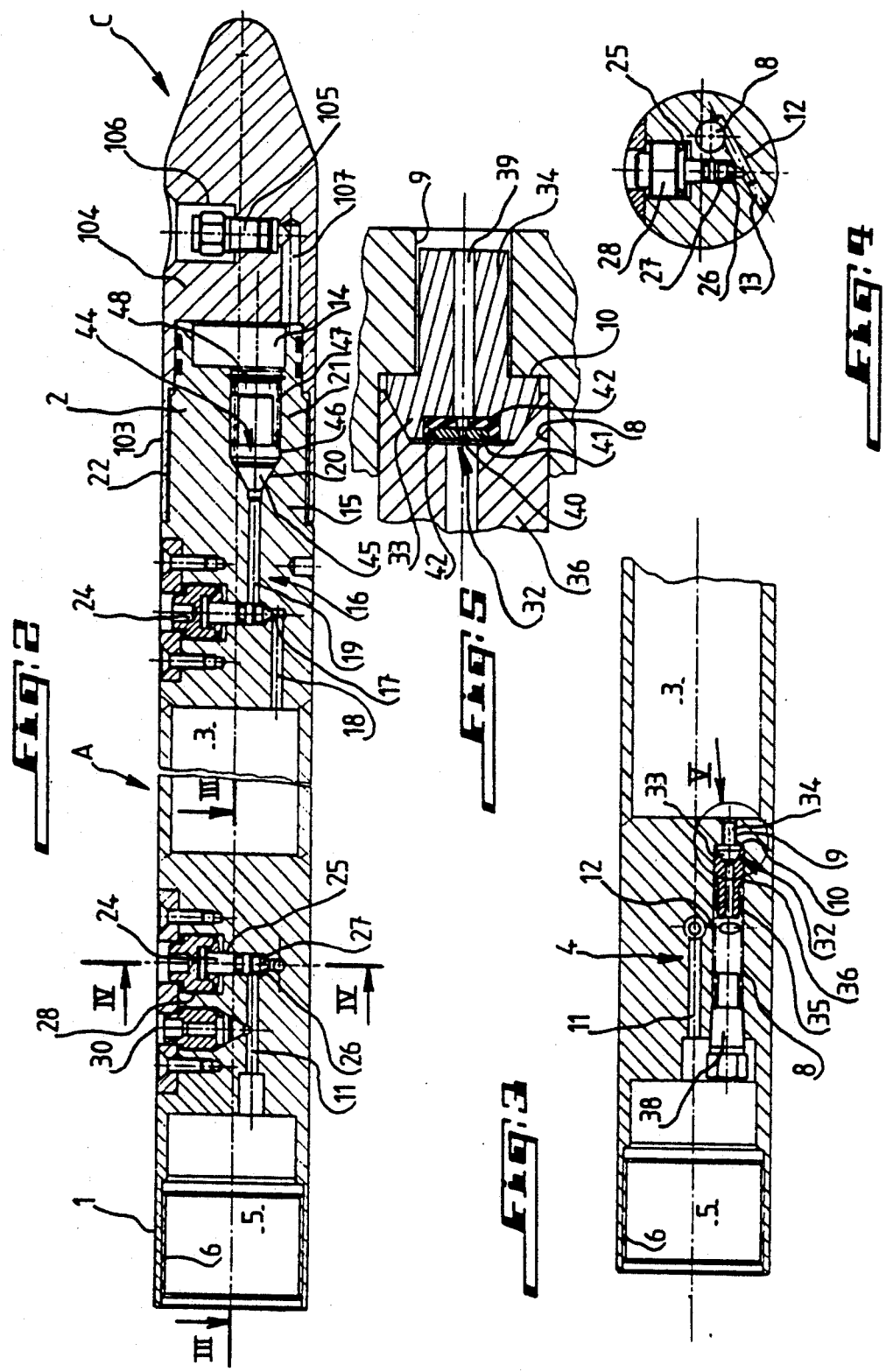

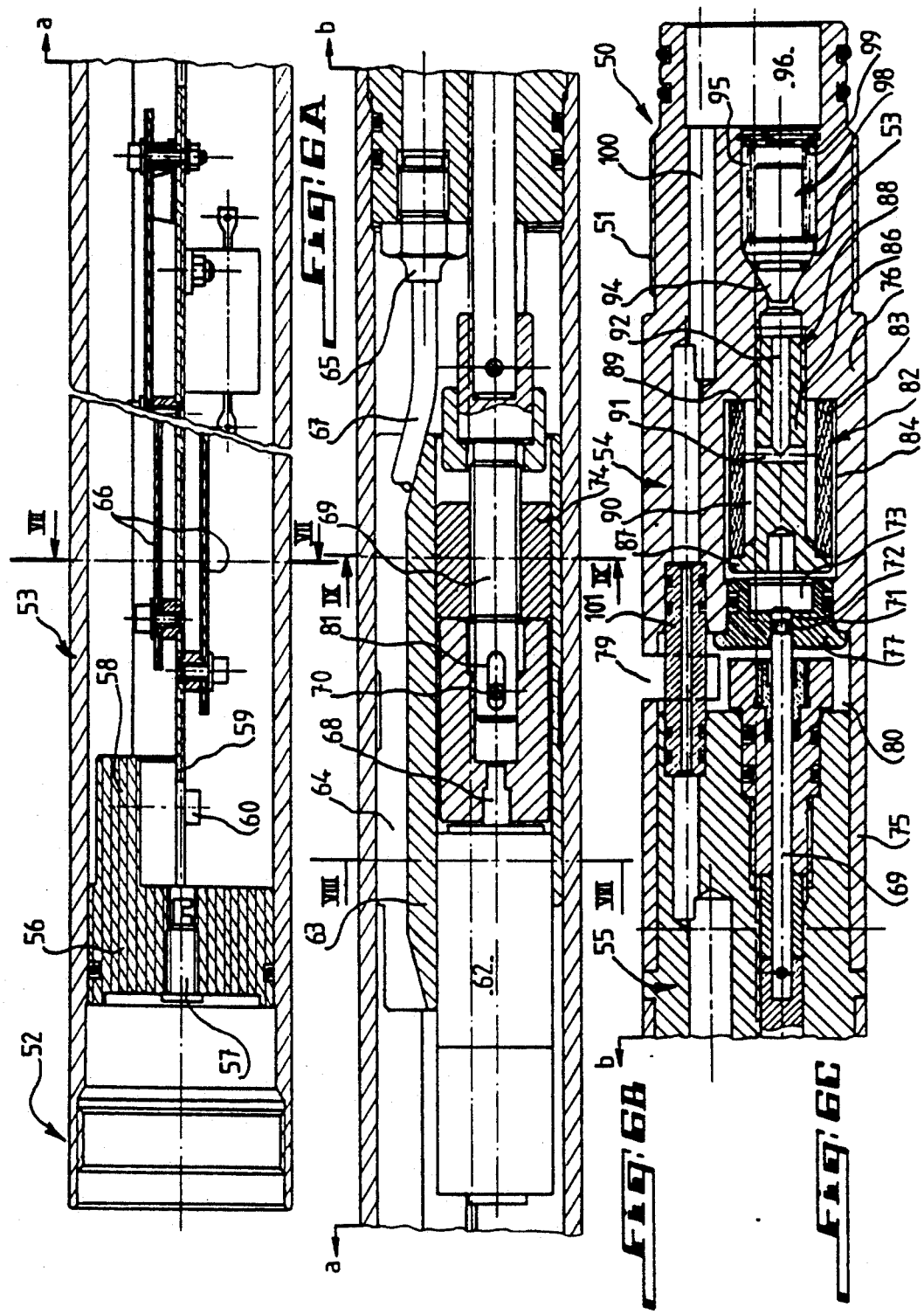

DEVICE FOR TAKING A FLUID SAMPLE FROM A WELL

BACKGROUND OF THE INVENTION

1. Field of the Invention

The invention relates to a method for taking a sample which is representative of the fluid, in particular of the gas, in a well at a given depth, and a sampling device for carrying out this method.

2. Description of the Related Art

There is already known a method which is based upon the use of a sampling device which comprises a bottle closed at one end and containing a piston. The bottle contains hydraulic oil separated from the fluid of the well by the piston. According to this method, the sampler is lowered to a desired depth in the well. To take a sample, the bottle is put in communication with a chamber provided inside the sampler and which is at atmospheric pressure. The hydraulic oil then flows from the bottle into the chamber through a pressure reducing valve. The piston moves back and slowly draws in the fluid from the well. The bottle closes when the piston reaches the bottom of the bottle.

This known method makes it possible to take a sample without varying its pressure or its temperature. It does not, however, guarantee the chemical integrity of the sample of the fluid of the well at the sampling depth. Indeed, the bottle is open at one end and may include a small amount of grease. Moreover, a film of hydraulic oil may remain on the bottle by the piston during the sampling.

The object of the invention is to provide a method and a sampling device which do not suffer from the problems discussed above.

SUMMARY OF THE INVENTION

The invention provides a method for taking a gaseous fluid sample from a well at a given depth according to which a bottle for taking a sample is lowered into the well to said predetermined depth. The bottle is caused to be filled and to be closed and this bottle is caused to be lifted to the surface.

Prior to the lowering of the bottle, a vacuum is provided within the latter. The evacuated bottle is lowered, and operated from the surface so that fluid in the well fills the bottle and causes the fluid to be retained within the bottle.

According to another feature of this method, a sampler device is used into which the bottle is removably mounted and which comprises a portion in which are arranged a means for filling the bottle and for control of a retaining means.

According to this method, the bottle is closed after its upward motion with the assistance of specific isolation means to allow for the storage of the sample within the bottle.

According to still a further feature, the aforesaid portion of the sampler is fitted with a remotely-controlled valve for taking samples and with a check valve for preventing the gas contained within the bottle from flowing out therefrom, and the sample taking is operated by opening the valve by remote control.

The sampler device for performing the method according to the invention comprises a sampler control portion including a probe detachably assembled to one end of a bottle portion. The sampler control portion comprises an inner space which communicates at one end with the outside through a passage-way allowing for the intake into this space of the fluid to be sampled. The inner space also communicates with channel which leads into a chamber for receiving the sample from the bottle. A sample-taking valve is provided for closing this channel, and is mounted in the device and provided with actuating means adapted to be remote-controlled from the surface.

According to another feature of the sampler device according to the invention, the device includes a device for retaining the sample within the chamber of the bottle, the device being a check valve fitted within the aforesaid channel downstream of the sample-taking valve.

According to still another feature, of the sampler, a filter is mounted in the fluid flow passageway within the probe, this filter being adapted to retain dust if present within the fluid.

According to still another feature, the aforesaid body comprises a pressure pick-up arranged so as to be exposed to the fluid downstream of the check valve, with which is associated a device for transmitting data relating to the measured pressure.

According to still a further feature, a nozzle having a small diameter, such as a jet, is mounted in an inner channel of the bottle which connects the chamber of the bottle to the inner channel of the aforesaid probe to provide for the expansion of the gaseous fluid to take place inside of the chamber.

According to still another feature of the invention, the bottle comprises chamber isolation means which are mounted within the inner channel thereof and is a shut-off valve for closing the channel.

BRIEF DESCRIPTION OF THE DRAWING(S)

The invention will be better understood and further objects, characterizing features, details and advantages thereof will appear more clearly from the following explanatory description with reference to the accompanying diagrammatic drawings given by way of a non-limiting example only, illustrating an embodiment of the invention and wherein:

FIG. 1 is a view in axial section through a sampler device according to the present invention;

FIG. 2 is a view in axial section of the portion A forming the bottle of the sampler according to FIG. 1;

FIG. 3 is a view in axial section taken upon the line III—III of FIG. 2;

FIG. 4 is a sectional view taken upon the line IV—IV of FIG. 2;

FIG. 5 is a view on a larger scale, with parts broken away, of the detail circled at V in FIG. 3;

FIGS. 6A, B, C are views in axial section of the control portion B of the sampler according to FIG. 1, shown as three lengths aligned axially in the manner shown by the letters a—a and b—b;

FIG. 7 is a sectional view taken upon the line VII—VII of FIG. 6A;

FIG. 8 is a view in section taken upon the line VIII—VIII of FIG. 6B;

FIG. 9 is a view in section taken upon the line IX—IX of FIG. 6B; and

FIG. 10 is a block diagram of the electrical arrangement of the sampler according to the invention.

DETAILED DESCRIPTION OF THE PREFERRED EMBODIMENT

Referring to FIG. 1, there is shown a sampler device according to the invention including three axially aligned and removably assembled parts, namely a part A forming a sample-taking bottle, a part B which is a separate, cylindrical body (a probe) which is detachably mounted onto the rear end of the bottle A and comprises the means and devices for operating the sampler device and for controlling the sampling, which is remote-controlled, a nose portion C is removably mounted onto the front end of the bottle A and terminates at a conical portion.

The bottle part A is shown in FIGS. 2 to 5. The bottle A essentially comprises a chamber 3 for taking samples which communicates through a duct or channel 4 (FIG. 3) with a cylindrical recess 5 formed in the top end 1 of the bottle, the axially open end portion of which is provided with a tapping 6. The duct 4 is a first axial duct length 8 which connects the chamber 3 and the recess 5. Duct 4 includes, in a portion adjacent to the chamber 3, a portion of smaller diameter 9 forming, radial ring shoulder 10, of an axial duct 11. Duct 11 extends from the recess 5 to some distance from the chamber 3. Portion 9 also forms a perpendicular duct length 12 which provides for the communication between the duct lengths 8 and 11. The latter are eccentric as shown on FIG. 4. The perpendicular duct 12 is obtained by drilling from the outer surface of the bottle down to a suitable depth in a skew direction for providing the connection. The duct is then closed at the open end by a plug shown at 13. On the other side of the chamber 3, i.e., towards the nose C, the bottle includes at its end 2 a cylindrical recess 14. Recess 14 axially opens outward, and the solid portion 15 located between this recess 14 and the chamber 3 has a communication channel 16 bored therethrough. Channel 16 includes two axial channel lengths 18, 19 extending inward from the area 15 from the chamber 3 and from the recess 14, respectively. Channel 16 also includes a transverse channel portion 17 which connects the channel lengths 18 and 19. Towards the recess 14, the channel 19 comprises an enlarged conical zone 20 followed by a cylindrical zone of greater diameter 21. The bottle includes an outer screw thread at end 22 allowing for the assembly of the nose C by screwing.

The bottle A comprises a number of members which provide for its operation. On either side of the chamber 3, there is a shut-off valve 24 which is mounted within a stepped radial bore 25 formed into the solid portion of the bottle at the respective transverse channel 12, 17. Valve 24 puts the channels 11, 12 and 17, 19 in communication. In the portion between these two channels, the bore is adapted to conform to the sealing seat 26 cooperating with a needle-shaped element 27 ending the shut-off valve 24. This valve is axially displaceable within the bore 25 by a threaded portion 28 by a suitable tool. The needles 27 and their suitable seats 26 form a metal-to-metal contact which provides for perfect fluid-tightness.

The bottle A moreover comprises between the shut-off valve 24 and the recess 5, i.e., within the upper portion of the bottle, a drain valve 30 also mounted in axially movable relationship within a radial bore extending from the outer cylindrical surface to the duct length 11. This drain valve may be made in any manner known per se and allows for a communication between the channel 11 and the outside.

The bottle A includes a nozzle of small diameter in channel 8 just at the inlet of the chamber 3. This nozzle (FIG. 5) is a jet shown at 32 which comprises a frusto-conical portion 33 and a cylindrical rod portion 34 with which the jet engages the portion of smaller diameter of the channel 9 while being pushed by the base of the frusto-conical portion 33 against the shoulder 10 of channel 8 by bearing element 36, arranged within the channel 8, the front face of which cooperates with the frusto-conical portion 33 of the jet 32, has a complementary or mating shape. The spring 35 bears at one end upon a suitable front face of the element 36, and at another, end upon a member 38 which is screwed into the channel 8 from the recess 5. Referring to FIG. 5, an axial duct 39 extends through this jet. At the opening of duct 39, towards the channel 8, there is a restriction, i.e., a calibrated hole 40, formed in a stone 41 within an axially bored supporting element 42 coaxially mounted into the end of the jet.

The bottle A includes a check valve 44 located in a lowered portion thereof at end 2 which is mounted within the frusto-conical portion 20 and the cylindrical portion 21 of the inner channel 19 of the bottle. As shown in FIG. 2, check valve 44 includes a frusto-conical head 45 which cooperates with the frusto-conical portion 20 of the channel 19 followed by a cylindrical portion 46 arranged in sliding relationship within the channel portion 21. Both frusto-conical surfaces 20 and 45, which are of complementary or mating shapes, are urged against each other by a spring 47 fitted in the channel portion 21 and bearing upon a bearing ring 48 arranged at the open end of the channel portion 21.

With reference to FIGS. 6A to 6C, there will hereinafter be described the probe portion B of the sampler according to the invention. Each figure shows the structure of a segment of the probe which are axially aligned along a—a in FIGS. 6A and 6B and b—b in FIGS. 6B and 6C. The left-hand end of FIG. 6A forms the upper end of the probe whereas the right hand end of FIG. 6C forms the lower end of the probe through which the latter is assembled to the upper end 1 of the bottle A. This lower end of the probe is shown at 50 and is provided with an outer, threaded cylindrical zone 51 allowing the bottle A to be screwed onto the probe. The upper end 52 of the probe B is connectable to a suspension device (not shown) of the sampler which may be fastened to a cable for lowering and lifting the sampler device in the well. The sampler includes three axially aligned separate parts, namely a tubular body or metal sheath 53, a lower cylindrical body 54 and an intermediate part 55 onto which the sheath 53 and the body 54 are fitted or slipped on.

The tubular body or sheath 53 includes at the top, i.e., at the end 52 of the probe, a plug 56 of electrically insulating material in the center of which is placed a female electrical connector 57 allowing for electrical connection with an electrical conductor which is the core of the suspension cable. The lower end of body 53 is connected to an inner cable (not shown) for supplying electrical energy to the various electrical devices arranged inside of the probe. The plug 56 includes an axial extension 58 with a cross-section shaped as an arc of a circle which allows for mounting a metal frame onto the plug 59 by screws shown at 60. Referring to FIG. 7, frame 59 is a plate arranged within the sheath 53 and extending axially, and is secured with its end to the casing of an electric motor-reducing gear set 62 which is fixedly mounted within an eccentric metal support body 63, as shown on FIG. 8. The support body 63 is fixedly mounted within the sheath 53, occupying the cross-section thereof and having an axial groove 64 on the periphery thereof. The frame 59 includes strengthening fins and houses electric cards 66 of printed circuits which control electric motor 62 and the electric circuits associated with pressure sensor 65 which controls the pressure of the fluid inside the bottle A, as will be explained later. Sensor 65 is connected by a cable or wire 67 extending through the axial groove 64 to the electric circuit associated therewith.

The rotary output shaft 68 of the motor 62 is rotationally connected to a threaded rod or spindle 69 through a pin 70 engaging elongated axial openings 81 of the rod 69 so as to allow an axial motion of the latter. The rod is screwed into a nut 74 which is fixedly mounted within the support body 63 (FIG. 9). The rod 69, which includes several axially aligned portions, extends axially through the intermediate portion 55 of the probe and includes at a free end thereof a packing joint 71, i.e., an O-ring seal. The latter shuts off or chokes the inlet port 72 of inner cylindrical chamber 73 of the probe.

The body 54 comprises an upper tubular portion 75 which it is axially fitted or slipped over the intermediate portion 55, and a solid lower portion 76 in which is formed the cylindrical chamber 73 from the front surface thereof towards the tubular portion 75. The port 72, which may be shut off or choked by the joint 71, includes an axial channel bored in a nut member 77 screwed into the chamber 73. The wall of the tubular portion 75 includes a cutout 79 which extends through this wall and extends over an arc of a circle, such as 90°. This cutout 79 forms an opening which provides a communication between the outside of the probe and an inner space 80 which the port 72 puts in communication with the chamber 73 if it is not shut off or choked by the joint 71. The latter and the nut 77 together with its hole 72 constitute the sample taking valve of the sample of the invention.

In the chamber 73 a filter device 82 is mounted which is a tubular filter element 83 that extends in coaxial relationship within the chamber 73 while leaving an annular space 84 between its outer cylindrical surface and the inner cylindrical face of the chamber. This tubular filter 83 includes a part 86 which closes the filter towards the port 72 and is screwed into a tapped cylindrical extension 88 of smaller diameter. The extension 88 forms, together with the chamber 73, a perpendicular radial surface 89 which closes the tubular filter 83 at its end. The supporting part 86 of the tubular filter 83 defines, together with the latter, a tubular inner space 90 which communicates through a diametral channel 91 located within the supporting part 86 with an axial channel 92 which opens into the extension chamber 88. The extension chamber 88 terminates at a transition portion having a smaller diameter which opens into an enlargement at 94 in a conical fashion. A cylindrical portion 95 opens into a cylindrical recess 96 formed in the lower end 50 of the probe. Referring to FIG. 6C, frusto-conical portion 94 is the seat of a check valve 98 with a frusto-conical head of the same kind as the check valve 44 in the lower portion of the bottle A. The movable body is urged or biased by a spring 99 onto the frusto-conical seat 94.

Referring to FIGS. 6B and 6C, there is shown the motor 62, the rod 69 for operating the sample taking valve and the chamber 73 together with its axial extension extending in coaxial but eccentric relationship within the probe. This arrangement makes it possible to provide within the lower body 54 and the intermediate portion 55 of the probe, a continuous, substantially axial channel 100 which extends from the recess 96 at the end of the probe to the pressure sensor 65. Channel 100 extends through the inner space 80, opening towards the outside through the opening 79 and passing into a tubular part 101 mounted at its two ends into the intermediate body 55 and the lower body 54, respectively.

Referring again to FIG. 2, there will hereinafter be described the front portion C of the sampler which forms the nose thereof. This portion C includes a tubular cylindrical rear portion 103 provided with an inner threading for assembling the portion C by screwing the same onto the front end of the bottle A. An intermediate zone 104 includes a sample taking valve 105 mounted within a radial stepped channel 106. Channel 106 extends from the outer cylindrical surface and opens inside zone 104 into a blind axial channel 107 which opens into the space defined by the tubular portion 103 that is in communication with the recess 14 of the inner end 2 of the bottle A. Valve 105 may be of any type known per se. The front portion of the nose part C of the sampler has a conical shape, as already mentioned.

Although FIG. 1 shows a sampler including a probe B, a bottle A and a nose portion C, it is designed so as to be capable of including several bottles, the second bottle being screwed at its tubular top end 1 onto the threaded bottom end 22 of the first bottle.

The sampler device according to the invention is operated and controlled from the surface of the well. Its electric devices are fed with electric energy, receive the operating orders and dialogue with an installation at the surface through an electric conductor provided within the suspension cable of the sampler. The supply of energy and the mode of dialoguing between the sampler and the surface will be described with reference to FIG. 10, which shows a simplified block diagram of the electric system of the sampler. The electric circuits of this system are integrated circuits located on the cards 66, 67 (FIG. 6A).

The electric system provides electric current to the motor 62 and the pressure detector 65 and removes information from the sensor 65 relating to the pressure prevailing within the chamber 3 of the bottle A. The motor and the sensor may be selectively controlled from the surface of the well. For this purpose, the invention includes a selective addressing mode through the strength of the direct current transmitted to the sampler. To recognize control orders, the electric system includes a control order decoding circuit which measures the probe feed current from the cable line at the input terminal shown at 110. A resistor 111 connects terminal 110 to the inner cable 112 of the probe. Referring to FIG. 10, the motor 62 is mounted between cable 112 and the ground through a switching element, preferably an electronic switch of the DMOS type operated by a first comparator 115. An input of comparator 115 is connected to the inner cable 112 whereas the other input is connected to the common terminal of two resistors 116, 117 of a voltage divider which further includes a third resistor 118, the voltage divider being mounted between the input terminal 110 and a resistor 119 which is grounded. A xenon diode is mounted on the series mounting of the three resistors 116 to 118. The pressure sensor 65 is connected through an amplifier 121 and a voltage-frequency converter 122 to the cable 112 through another switching element 123 also preferably of the DMOS type. The latter is operated by a second comparator 124 connected by an input to the inner cable 112 and by another input to the common terminal of the resistors 117 and 118.

Both comparators 115, 124 form the decoding circuit discussed above and arrange arranged so as to be energized when the current sent through the cable to the input terminal 110 exceeds respective predetermined threshold values.

The operation of the sampler device according to the present invention will now be described.

Before lowering the sampler into the well a vacuum is established within the chamber 3 of the bottle A. The sample taking valve is closed, i.e., the joint 71 at the tip of the axially movable rod 69 actuated by the motor 62 is inserted into the port 72 and thus isolates the chamber 73 from the outside. During the lowering of the device into the well, it is possible to constantly control the vacuum through the measurement of the pressure inside of the chamber by the pressure sensor 65. A direct current stronger than a first threshold value, for instance of 190 mA, may be sent through the cable thereby energizing the comparator 124 which then produces a signal for opening the switch 123. This allows signals representative of the pressure measured by the sensor 65 to be sent to the cable which transmits them to the surface of the well. The values of the voltages produced at the output of the sensor 65 and amplified by the amplifier 121 are converted into suitable frequency values by the voltage-frequency converter 122.

Initiation of the sample taking when the sampler has reached the desired depth is achieved when a current higher than a second threshold value, for instance of 190 mA, may be sent though the cable thereby energizing the comparator 124 which then produces a signal for opening the switch 123. This allows signals representative of the pressure measured by the sensor 65 to be sent to the cable which transmits them to the surface of the well. The values of the voltages produced at the output of the sensor 65 and amplified by the amplifier 121 are converted into suitable frequency values by the voltage-frequency converter 122.

Initiation of the sample taking when the sampler has reached the desired depth is achieved when a current higher than a second threshold value, for instance of 240 mA is detected. The comparator 115 produces, in response to this signal, a signal which is applied to the switch 114 which closes or makes a circuit feeding the motor 62. Rotation of the output shaft 68 of the motor causes the rod which carries the joint 71 to move in axial relationship for retracting this joint from the port 72 thereby providing a communication between the chamber 73 inside of the probe and the outside through the opening 79. Thus, the fluid, and more specifically the gas, contained in the well may enter the chamber 73 and flow into the chamber 3 of the bottle A while passing through the filter 82, the check valve 98 and the expansion nozzle or jet 33, the shut-off valve 24 being open. The function of the jet is to limit the gas flow rate upstream and thus avoid condensation of heavy fractions before the chamber 3 of the sampler. The jet is located for that purpose just at the inlet of the bottle. The expansion therefore takes place inside of the bottle and, although this expansion possibly produces phase changes, the stoichiometry of the various components of the gas is strictly retained. Indeed the volume of the inner space upstream of the chamber 3 is negligible with respect to the volume of the latter. The filter 82 retains the dust possibly present within the gas flowing into the chamber 3 which dust could interfere with the closing of the check valve 98 or damage the various valves. Measurement of the pressure inside of the chamber 3 by the pressure sensor 65 continues to be carried out during this period. The gas contained within the chamber 3 remains trapped since the check valves 98 and 44 located on either side of the chamber 3 prevent the gases from flowing out of the chamber. The sample taking valve 105 within the nose C of the sampler is of course also closed.

Under such circumstances the sample may be lifted up to the surface of the well where it will be possible to close the shut-off valves 24 of the bottle A located on either side of the chamber 3 and to remove the bottle from the sampler. The sample could thus be stored inside of the bottle for a subsequent analysis of its content. The sample may be removed from the device by opening the sample taking valve 105 which fits into the nose C of the sampler.

Drain valve 30 makes it possible to unscrew the bottle A from the probe B when the bottle is under pressure either to completely empty it after the closure of the shut-off valve or to drain the volume between the check valve 98 and the bottle. Shut-off valve 24 located within the lower portio of the bottle A allows for aeration of a vacuum before taking the sample and for transferring the sample.

As already explained above, the design of the sampler in several independent parts allows for mounting several bottles A in series within the same sampler. The lower bottle would then connect to the nose portion C.

Although the present invention has been described in connection with a plurality of preferred embodiments thereof, many other variations and modifications will now before apparent to those skilled in the art. It is preferred, therefore, that the present invention be limited not by the specific disclosure herein, but only by the appended claims.

What is claimed is:

1. A sampler device for taking a sample of gaseous fluid contained within a well, comprising:

a bottle portion having a lower end and an upper end;

a sampler control portion removably attachable to said upper end of said bottle portion, said sampler portion including an inner space communicating at a first end with said gaseous fluid through a passage-way allowing flow of said gaseous fluid into said inner space and at a second end through an inner channel with a sample receiving chamber;

a valve mounted in said inner channel for closing or opening said channel, wherein, prior to the taking of the sample of gaseous fluid, said valve is closed and a vacuum is established within said sample receiving chamber;

means for actuating said valve, said actuating means being remotely controlled from the surface of said well and comprising a remote-controlled motor having a rotary output shaft extending in parallel relationship to the axis of the sampler device, means for transforming rotary motion of said motor shaft to axial motion of a rod displaceable in the direction of the axis of said sampler device, said valve comprising a movable valve closing and opening element mounted on said rod and axially displaceable therewith within said sampler device; and a jet nozzle mounted within said inner channel at the inlet of said sample receiving chamber, said jet nozzle having a diameter smaller than the diameter of said inner channel for limiting the flow rate of the fluid flowing through said inner channel into said sample receiving chamber, thereby preventing condensation of heavy fluid fractions at said sample receiving chamber inlet when said valve is opened.

2. A sampler device according to claim 1, further comprising means for retaining said sample within said chamber of said bottle comprising a check valve mounted in said channel downstream of said valve.

3. A sampler device according to claim 1, further comprising a filter mounted in said channel for retaining dust contained within said fluid.

4. A sampler device according to claim 1, further comprising a pressure sensor arranged so as to be exposed to said fluid and a device for transmitting data relating to measured pressure.

5. A sampler device according to claim 1, further comprising means for isolating the chamber comprising a shutoff valve for closing said channel.

6. A sampler device according to claim 1, further comprising a recess located in said bottle lower end, said recess being connected to said chamber through a second inner channel, a channel closing valve being associated with the second channel.

7. A sampler device according to claim 6, further comprising a check valve mounted within said second channel between the channel closing valve and said recess.

8. A sampler device according to claim 7, wherein said lower end of said bottle is removably attachable to an upper end of another bottle, chambers of both bottles being in communication.

9. A sampler device according to claim 1, further comprising a nose removably attached in an axially aligned relationship to said lower end of said bottle, said nose comprising a third inner channel which opens into an outer face of said nose through a connecting port for transferring samples trapped within said bottle, a sample-taking valve being arranged within said third inner channel.

10. A sampler device according to claim 1, wherein said sampler control portion, valve actuation means and motor are supplied with electric energy and electrically controlled through a cable from which said sampler device is suspended, electric circuit means for receiving and emission of electric signals being located within said sampler device.

11. A sampler device according to claim 10, wherein said sampler control portion, valve actuation means and motor are selectively addressable by a coded control signal of a direct current of specific strength through said cable, the circuit means comprising decoders.

12. A sampler device according to claim 10, wherein said circuit means comprises an interface sensor including a voltage-frequency converter.

13. A sampler device for taking a sample of gaseous fluid contained within a well, comprising:

a bottle portion having a lower end and an upper end;

a sampler control portion removably attachable to said upper end of said bottle portion, said sampler portion including an inner space communicating at a first end with said gaseous fluid through a passage-way allowing flow of gaseous fluid into said inner space and a second end through an inner channel with a sample receiving chamber;

a valve mounted in said inner channel for closing or opening said channel, wherein, prior to the taking of the sample of gaseous fluid, said valve is closed and a vacuum is established within said sample receiving chamber;

means for actuating said valve, said actuating means being remotely controlled from the surface of said well and comprising a remote-controlled motor having a rotary output shaft extending in parallel relationship to the axis of the sampler device, means for transforming rotary motion of said motor shaft to axial motion of a rod displaceable in the direction of the axis of said sampler device, said rotary shaft and said rod being axially aligned with each other, said valve comprising a movable valve closing and opening element mounted on said rod and axially displaceable therewith within said sampler device, said means for transforming the rotary motion of the motor shaft to an axial motion of said rod comprising a nut mounted stationary in said sampler device and through which said rod extends axially with said rod having on a peripheral surface thereof a threaded portion for cooperating with an inner thread of said nut, said rod being rotatively secured to said rotary motor shaft but axially movable with respect to said motor shaft; and a jet nozzle mounted within said inner channel at the inlet of said sample receiving chamber, said jet nozzle having a diameter smaller than the diameter of said inner channel for limiting the flow rate of the fluid flowing through said inner channel into said sample receiving chamber, thereby preventing condensation of heavy fluid fractions at said sample receiving chamber inlet when said valve is opened.

* * * * *